United States Patent
Karube et al.

(10) Patent No.: US 11,981,883 B2
(45) Date of Patent: May 14, 2024

(54) COMPOSITION CONTAINING 1,2-DICHLORO-3,3,3-TRIFLUOROPROPENE

(71) Applicant: DAIKIN INDUSTRIES, LTD., Osaka (JP)

(72) Inventors: Daisuke Karube, Osaka (JP); Yuuko Tsutsui, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 612 days.

(21) Appl. No.: 17/267,199

(22) PCT Filed: Aug. 5, 2019

(86) PCT No.: PCT/JP2019/030733
§ 371 (c)(1),
(2) Date: Feb. 9, 2021

(87) PCT Pub. No.: WO2020/031962
PCT Pub. Date: Feb. 13, 2020

(65) Prior Publication Data
US 2021/0301224 A1  Sep. 30, 2021

(30) Foreign Application Priority Data
Aug. 10, 2018 (JP) .................. 2018-151836

(51) Int. Cl.
| | | |
|---|---|---|
| *C11D 3/24* | (2006.01) |
| *B08B 3/04* | (2006.01) |
| *B08B 3/08* | (2006.01) |
| *C07C 21/18* | (2006.01) |
| *C11D 7/28* | (2006.01) |
| *C11D 7/30* | (2006.01) |
| *C11D 7/50* | (2006.01) |
| *C11D 9/28* | (2006.01) |

(52) U.S. Cl.
CPC .............. *C11D 7/5018* (2013.01); *B08B 3/08* (2013.01); *C11D 7/30* (2013.01); *B08B 2220/00* (2013.01)

(58) Field of Classification Search
CPC .. C11D 3/24; C11D 3/245; C11D 7/28; C11D 7/30; C11D 7/5018; C11D 9/28; C07C 21/18; B08B 3/04; B08B 3/08
See application file for complete search history.

(56) References Cited

U.S. PATENT DOCUMENTS

| | | |
|---|---|---|
| 2013/0146100 A1 | 6/2013 | Saito et al. |
| 2017/0321167 A1 | 11/2017 | Imura et al. |
| 2018/0134640 A1 | 5/2018 | Nakamura et al. |
| 2018/0265821 A1 | 9/2018 | Imura et al. |
| 2021/0238507 A1* | 8/2021 | Osafune .............. C09D 171/00 |

FOREIGN PATENT DOCUMENTS

| | | | |
|---|---|---|---|
| CN | 102971836 | 3/2013 |
| JP | 2-221388 | 9/1990 |
| JP | 2009-514251 | 4/2009 |
| JP | 2016-141730 | 8/2016 |
| JP | 2016-169256 | 9/2016 |
| JP | 2017-43742 | 3/2017 |
| WO | 2005/044969 | 5/2005 |
| WO | WO 2005/044969 | * 5/2005 | .............. C11D 7/50 |
| WO | 2007/053673 | 5/2007 |
| WO | 2016/080133 | 5/2016 |
| WO | 2016/125550 | 8/2016 |
| WO | 2017/018010 | 2/2017 |
| WO | 2019/078352 | 4/2019 |
| WO | 2019/117100 | 6/2019 |
| WO | 2020/022478 | 1/2020 |

OTHER PUBLICATIONS

International Search Report dated Sep. 17, 2019 in International (PCT) Application No. PCT/JP2019/030733.
Extended European Search Report dated May 24, 2022 in European Patent Application No. 19847921.4.
International Preliminary Report on Patentability dated Feb. 16, 2021 in International (PCT) Application No. PCT/JP2019/030733.

* cited by examiner

*Primary Examiner* — Brian P Mruk
(74) *Attorney, Agent, or Firm* — Wenderoth, Lind & Ponack, L.L.P.

(57) ABSTRACT

A composition containing 1,2-dichloro-3,3,3-trifluoropropene (HCFO-1223xd) and a fluorine-based oil.

7 Claims, No Drawings

COMPOSITION CONTAINING 1,2-DICHLORO-3,3,3-TRIFLUOROPROPENE

TECHNICAL FIELD

The present disclosure relates to a composition comprising 1,2-dichloro-3,3,3-trifluoropropene (hereinafter also simply referred to as "HCFO-1223xd").

BACKGROUND ART

With implementation of stricter regulations on hydrofluorocarbons in 2020, there is an urgent need to develop an alternative for hydrofluorocarbons. In particular, considering the environmental burden, which is a major issue in use of hydrofluorocarbons, an alternative that has low global warming potential and low ozone depletion potential as well as low biotoxicity is desired. In such circumstances, hydrochlorofluoroolefins (hereinafter also referred to as "HCFO") have been attracting attention.

Patent Literature (PTL) 1 discloses a lubricant composition containing HCFO-1223za, which is one type of HCFO.

Patent Literature (PTL) 2 and Patent Literature (PTL) 3 disclose that HCFO-1223xd, which is another type of HCFO, is useful as a cleaning agent.

CITATION LIST

PATENT LITERATURE

PTL 1: JP2016-169256A
PTL 2: JPH2-221388A
PTL 3: JP2016-141730A

SUMMARY OF INVENTION

TECHNICAL PROBLEM

In view of the above circumstances, an object of the present disclosure is to provide a composition containing HCFO-1223xd and an oil that are highly compatible with each other; or an HCFO-1223xd-containing composition for solvents, diluents, or cleaners to remove fluorine-based oil.

SOLUTION TO PROBLEM

The present inventors conducted extensive research to achieve the above object. As a result, the inventors found that HCFO-1223xd is highly compatible with fluorine-based oil and that a composition containing HCFO-1223xd can be provided as a composition for solvents, lubricants, or cleaners to remove fluorine-based oil. The inventors continued their research based on this finding and finally accomplished the present disclosure.

More specifically, the present disclosure provides the following compositions.

Item 1.
A composition comprising 1,2-dichloro-3,3,3-trifluoropropene (HCFO-1223xd) and a fluorine-based oil.

Item 2a.
A composition for solvents or diluents, the composition comprising 1,2-dichloro-3,3,3-trifluoropropene (HCFO-1223xd).

Item 2b.
A solvent, a lubricant, or a cleaner for removing fluorine-based oil, the solvent, lubricant, or cleaner comprising 1,2-dichloro-3,3,3-trifluoropropene (HCFO-1223xd).

Item 3.
The composition according to Item 2a, wherein the composition comprises an oil.

Item 4.
The composition according to Item 3, wherein the oil is a fluorine-based oil.

Item 5.
The composition according to Item 1 or 4, wherein the mass ratio of the HCFO-1223xd to the fluorine-based oil is such that the ratio of the total mass of the HCFO-1223xd and the fluorine-based oil to the mass of the fluorine-based oil is in the range of 100:0.1 to 100:80.

Item 6.
The composition according to any one of Items 1, 4, and 6, wherein the fluorine-based oil is at least one member selected from the group consisting of perfluoropolyethers, hydrofluoropolyethers, and low polymers of chlorotrifluoroethylene.

Item 7.
The composition according to any one of Items 1 and 4 to 6, wherein the fluorine-based oil has a kinematic viscosity at 40° C. of 15 mm$^2$/s or more.

Item 8.
A composition for cleaners to remove a fluorine-based oil, the composition comprising 1,2-dichloro-3,3,3-trifluoropropene (HCFO-1223xd).

Item 9.
A cleaning method using a cleaner comprising 1,2-dichloro-3,3,3-trifluoropropene (HCFO-1223xd) to remove a fluorine-based oil.

ADVANTAGEOUS EFFECTS OF INVENTION

According to the present disclosure, there can be provided a composition comprising HCFO-1223xd and an oil that are highly compatible with each other, or an HCFO-1223xd-containing composition for solvents or diluents.

DESCRIPTION OF EMBODIMENTS

The composition according to the present disclosure is a composition containing 1,2-dichloro-3,3,3-trifluoropropene (HCFO-1223xd) and a fluorine-based oil.

The fluorine-based oil to be used is not particularly limited and can be any of a wide variety of known fluorine-based oils. To ensure sufficient lubricity and coating film strength, the fluorine-based oil to be used preferably has a kinematic viscosity at 40° C. of 15 mm$^2$/s or more, and more preferably 30 mm$^2$/s or more. Specifically, at least one member selected from the group consisting of perfluoropolyethers, hydrofluoropolyethers, and low polymers of chlorotrifluoroethylene can be used. The term "low polymer" as used herein is defined as a polymer having an average molecular weight of about 10000 or less.

The term "clear" as used herein is defined as a state in which the composition is in the state of being uniform and not turbid.

In view of exhibiting effects of fluorine-based oil dissolved and obtaining a uniform composition, the content of the fluorine-based oil is preferably such that the mass ratio of the total mass of HCFO-1223xd and fluorine-based oil to the mass of fluorine-based oil is in the range of 100:0.1 to 100:80, more preferably 100:1 to 100:80, even more preferably 100:4 to 100:80, still even more preferably 100:25 to 100:80, and particularly preferably 100:50 to 100:80.

Until now, it has not been known that HCFO-1223xd and fluorine-based oil are highly compatible with each other. The inventors of the present disclosure repeated trial and error on combinations of a huge number of HCFOs and oils. As a result, the inventors surprisingly found that when a combination of HCFO-1223xd and fluorine-based oil is used, even if the fluorine-based oil content is set to a high concentration as described above, no turbidity occurs and a clear composition can be obtained due to high compatibility between the two.

Further, the composition according to the present disclosure is advantageous in that the composition creates much less environmental burden due to its low global warming potential and low ozone depletion potential, and also has low biotoxicity.

The composition according to the present disclosure as described above can be used as a solvent and a diluent due to its excellent compatibility between HCFO-1223xd and fluorine-based oil. In particular, due to excellent compatibility between HCFO-1223xd and fluorine-based oil and a moderately high boiling point of the mixture of HCFO-1223xd and fluorine-based oil, the composition can be preferably used as a solvent for coating solutions. Further, in order to obtain such excellent compatibility, the composition according to the present disclosure preferably has a boiling point of −10 to 60° C., and more preferably 0 to 40° C. When the composition is used as a solvent or a cleaner, if the boiling point of the composition is within this temperature range, good solubility is obtained and evaporation can be further inhibited.

The solvent as used herein is defined as a medium for dissolving a substance, such as oil. The diluent as used herein is defined as a solvent for dissolving and diluting a substance, such as oil, that has problems when used as is, such as low fluidity and poor processability, and low stability, to thereby solve the problems.

The present disclosure includes a composition for solvents, lubricants, or cleaners to remove fluorine-based oil, the composition containing 1,2-dichloro-3,3,3-trifluoropropene (HCFO-1223xd) (or a solvent, a lubricant, or a cleaner for removing fluorine-based oil, each containing 1,2-dichloro-3,3,3-trifluoropropene (HCFO-1223xd)).

The composition for solvents or diluents preferably contains oil.

The oil to be used is not particularly limited and can be any of a wide variety of oils that are known to be used for solvents or diluents. More specifically, at least one member selected from the group consisting of fluorine-based oils, silicone-based oils, mineral-based oils, and ester-based oils can be used.

Examples of usable fluorine-based oils include, but are not limited to, a wide variety of known fluorine-based oils. To ensure sufficient lubricity and coating film strength, the fluorine-based oil to be used preferably has a kinematic viscosity at 40° C. of 15 mm$^2$/s or more, and more preferably 30 mm$^2$/s or more. Specifically, at least one member selected from the group consisting of perfluoropolyethers, hydrofluoropolyethers, and low polymers of chlorotrifluoroethylene can be used. The low polymer as used herein is defined as a polymer having an average molecular weight of about 10000 or less. Examples of the fluorine-based oil further include fluorosilicone-based oils in which a fluoroalkyl group is introduced into an end or a side chain of silicone.

Examples of usable silicone-based oils include, but are not limited to, a wide variety of known silicone-based oils. More specifically, at least one member selected from the group consisting of dimethyl silicone, methyl phenyl silicone, and modified silicone that has an organic group introduced into an end or a side chain of silicone can be used.

Examples of usable mineral oils include, but are not limited to, a wide variety of known mineral oils. More specifically, at least one member selected from the group consisting of paraffin-based oils, naphthenic oils, and poly-α-olefin-based oils can be used.

Examples of usable ester-based oils include, but are not limited to, a wide variety of known ester-based oils. More specifically, at least one member selected from the group consisting of polyol ester-based oils, diester-based oils, and complex ester-based oils can be used.

However, among the oils mentioned above, it is preferable to use a fluorine-based oil because of its excellent compatibility with HCFO-1233xd. A combination of HCFO-1223xd and fluorine-containing oil that are highly compatible with each other enables the production of a stable composition that is uniform and does not become turbid in a wide range of oil concentration, temperature, or other conditions, thus obtaining excellent physical properties as a composition for solvents or diluents.

When using a combination of HCFO-1223xd and a fluorine-based oil that are highly compatible with each other as described above, the composition for solvents or diluents according to the present disclosure can be formed as a clear composition for solvents or a clear composition for diluents. Further, in order to obtain such excellent compatibility, the composition for solvents, diluents, or cleaners to remove fluorine-based oil according to the present disclosure preferably has a boiling point of −10 to 60° C., and more preferably 0 to 40° C.

Further, since the composition for solvents containing HCFO-1223xd and fluorine-based oil has a moderately high boiling point, the composition can be suitably used as a solvent for coating solutions.

For exhibiting effects of fluorine-based oil dissolved and obtaining a uniform composition, the content of the fluorine-based oil is preferably such that the mass ratio of the total mass of HCFO-1223xd and fluorine-based oil to the mass of fluorine-based oil is in the range of 100:0.1 to 100:80, more preferably in the range of 100:1 to 100:80, even more preferably in the range of 100:4 to 100:80, still even more preferably in the range of 100:25 to 100:80, and particularly preferably in the range of 100:50 to 100:80.

The composition containing 1,2-dichloro-3,3,3-trifluoropropene (HCFO-1223xd) and fluorine-based oil, or the HCFO-1223xd-containing composition for solvents, diluents, or cleaners to remove fluorine-based oil according to the present disclosure can further contain one or more other solvents. Such other solvents are added, for example, in order to further improve the solubility of the target substance.

Such other solvents are not particularly limited and can be selected from a wide variety of solvents. Examples of such solvents include 1,2-dichloroethylene, isopropanol, and the like. The composition according to the present disclosure preferably contains such other solvents in an amount of 0.1 to 50 mass %, preferably 1 to 10 mass %, relative to the total amount of the composition defined as 100 mass %.

The composition containing 1,2-dichloro-3,3,3-trifluoropropene (HCFO-1223xd) and fluorine-based oil, or the HCFO-1223xd-containing composition for solvents, diluents, or cleaners to remove fluorine-based oil can further contain other components. Such other components are, for example, one or more members selected from the group consisting of antioxidants, stabilizers, preservatives, surfactants, and the like.

The composition containing 1,2-dichloro-3,3,3-trifluoropropene (HCFO-1223xd) and fluorine-based oil, or the HCFO-1223xd-containing composition for solvents, diluents, or cleaners to remove fluorine-based oil can further contain a surfactant or the like, in addition to the above components.

The composition according to the present disclosure preferably contains HCFO-1223xd and fluorine-based oil in a total amount of 1 to 100 mass %, more preferably 50 to 100 mass %, and even more preferably 80 to 100 mass %, based on the total amount of the composition defined as 100 mass %.

Further, the composition for solvents, diluents, or cleaners to remove fluorine-based oil according to the present disclosure is advantageous in that the composition not only creates much less environmental burden due to low global warming potential and low ozone layer depletion potential but also has low biotoxicity.

The HCFO-1223xd as used herein is defined to include either its E-isomer or Z-isomer, or both isomers. When the HCFO-1223xd contains both the E-isomer and Z-isomer, their content ratio is not particularly limited, and does not affect the problem solution achieved by the composition according to the present disclosure. Alternatively, the HCFO-1223xd can be either the E-isomer or the Z-isomer. The mass ratio of the E-isomer to the Z-isomer can be, for example, in the range of 0:100 to 40:60.

Further, the present disclosure includes a cleaning method using a cleaner comprising 1,2-dichloro-3,3,3-trifluoropropene (HCFO-1223xd) in order to remove a fluorine-based oil.

The fluorine-based oil to be removed is not particularly limited and examples include those mentioned above.

If necessary, the cleaner may further contain at least one member selected from the group consisting of solvents, antioxidants, stabilizers, preservatives, surfactants, and the like, in addition to HCFO-1223xd. Such solvents, antioxidants, stabilizers, preservatives, and surfactants are not particularly limited and can be any of a wide variety of those known.

Embodiments according to the present disclosure are described above. However, the present invention is not limited to these embodiments. Various modifications can be made without departing from the gist of the present disclosure.

EXAMPLES

The embodiments of the present invention are described in more detail below based on the Examples; however, the present invention is not limited to these.

Compatibility

Example 1
The solubility of fluorine-based oil (perflopolyether, Demnum S-65, produced by Daikin Industries, Ltd.) in HCFO-1223xd was measured. The fluorine-based oil was dissolved at 25° C. in an amount of 65 mass %, based on the total mass of HCFO-1223xd and fluorine-based oil. The kinematic viscosity of the fluorine-based oil at 40° C. was 65 mm$^2$/s.

Example 2
The solubility of silicone-based oil (dimethyl silicone oil, KF-96M, produced by Shin-Etsu Chemical Co., Ltd.) in HCFO-1223xd was measured. The silicone-based oil was dissolved at 25° C. in an amount of 80 mass %, based on the total mass of HCFO-1223xd and fluorine-based oil.

Comparative Example 1
The solubility of fluorine-based oil (Demnum S-65, produced by Daikin Industries, Ltd.) in HCFO-1223zd (Z-isomer) was measured. The fluorine-based oil did not dissolve at 25° C. but was separated from HCFO-1223zd.

Coating Properties

Example 3
Fluorine-based oil (Demnum S-65, produced by Daikin Industries, Ltd.) was added as a lubricant to HCFO-1223xd in an amount to achieve a composition ratio of HCFO-1223xd to fluorine-based oil of 97 mass % to 3 mass %. The obtained solution was applied to an aluminum substrate to form a coating having an average thickness of 0.5 mm. The coating was then air-dried at 24 to 27° C., thus obtaining a uniform lubricant coating film.

Stability

Example 4
Fluorine-based oil (Demnum S-65, produced by Daikin Industries, Ltd.) was added as a lubricant to HCFO-1223xd in an amount to achieve a composition ratio of HCFO-1223xd to fluorine-based oil of 50 mass % to 50 mass %. The obtained solution was allowed to stand at 25° C. for 7 days. No changes in color, precipitation, etc. were observed.

Cleaning Power

Example 5
Glass test pieces, each 50 mm×5 mm×2 mm, which had been immersed in fluorine oil (Demnum S-65, produced by Daikin Industries, Ltd.), were immersed in 100 ml of HCFO-1223xd at 25° C. for 1 minute and then taken out. The fluorine oil remaining on the test pieces was thereby removed.

Biotoxicity

Example 6
A 4-hour single-inhalation exposure test was performed on rats by using a mist of HCFO-1223xd according to the OECD Guideline No. 436. No death of the rats was observed even when the rats were exposed to a mist of HCFO-1223xd at a concentration of 5 mg/L. HCFO-1223xd was found to have low acute toxicity.

The invention claimed is:
1. A composition for solvents or diluents, the composition comprising 1,2-dichloro-3,3,3-trifluoropropene (HCFO-1223xd) and an oil,
   wherein the oil is a fluorine-based oil, and
   wherein the mass ratio of the HCFO-1223xd to the fluorine-based oil is such that the ratio of the total mass of the HCFO-1223xd and the fluorine-based oil to the mass of the fluorine-based oil is in the range of 100:0.1 to 100:4.
2. The composition according to claim 1, wherein the fluorine-based oil is at least one member selected from the group consisting of perfluoropolyethers, hydrofluoropolyethers, and low polymers of chlorotrifluoroethylene.

3. The composition according to claim 1, wherein the fluorine-based oil has a kinematic viscosity at 40° C. of 15 mm²/s or more.

4. A method of cleaning a surface comprising a fluorine-based oil, the method comprising applying a a composition comprising 1,2-dichloro-3,3,3-trifluoropropene (HCFO-1233xd) to the surface comprising the fluorine-based oil, wherein the mass ratio of the HCFO-1223xd to the fluorine-based oil is such that the ratio of the total mass of the HCFO-1223xd and the fluorine-based oil to the mass of the fluorine-based oil is in the range of 100:0.1 to 100:4.

5. The composition according to claim 1, wherein the fluorine-based oil is at least one member selected from the group consisting of perfluoropolyethers, hydrofluoropolyethers, and low polymers of chlorotrifluoroethylene.

6. The composition according to claim 1, wherein the fluorine-based oil has a kinematic viscosity at 40° C. of 15 mm²/s or more.

7. The composition according to claim 2, wherein the fluorine-based oil has a kinematic viscosity at 40° C. of 15 mm²/s or more.

\* \* \* \* \*